United States Patent [19]

Heil

[11] Patent Number: 5,033,960
[45] Date of Patent: Jul. 23, 1991

[54] DENTAL HANDPIECE CONNECTOR ASSEMBLY WITH REPLACEABLE AIR-COOLED LAMP AND INSERTION/EXTRACTION TOOL THEREFOR

[75] Inventor: Donald J. Heil, Lake Villa, Ill.

[73] Assignee: Midwest Dental Products Corporation, Des Plaines, Ill.

[21] Appl. No.: 608,723

[22] Filed: Nov. 5, 1990

[51] Int. Cl.$^5$ .............................................. A61C 1/00
[52] U.S. Cl. .................................... 433/29; 433/126
[58] Field of Search .................. 433/29, 126; 81/3.8; 439/374, 380

[56] References Cited

U.S. PATENT DOCUMENTS

| | | | |
|---|---|---|---|
| 2,454,878 | 11/1948 | Marler | 81/3.8 |
| 4,330,274 | 5/1982 | Friedman et al. | 433/29 |
| 4,477,252 | 10/1984 | Lieb et al. | 433/126 |
| 4,514,169 | 4/1985 | Strohmaier | 433/29 |
| 4,600,384 | 7/1986 | Olsen | 433/29 |

Primary Examiner—Cary E. Stone
Attorney, Agent, or Firm—Tilton, Fallon, Lungmus

[57] ABSTRACT

A connector for attaching a supply hose to a dental handpiece, the connector including a generally cylindrical body having a longitudinally-extending socket containing a lamp for directing light towards a fiberoptic light conductor of the handpiece during operation. The body also includes an exhaust air passage that extends alongside the socket and communicates with that socket through a slot extending substantially the full length of the socket. The lamp includes bulb and base portions with the base portion having a lug projecting radially outwardly through the slot into the exhaust air passage. A tool has stem and head portions insertable into the exhaust air passage for engaging the lug when extraction of the lamp is desired.

20 Claims, 2 Drawing Sheets

DENTAL HANDPIECE CONNECTOR ASSEMBLY WITH REPLACEABLE AIR-COOLED LAMP AND INSERTION/EXTRACTION TOOL THEREFOR

BACKGROUND AND SUMMARY

Dental handpieces (and similar power-operated hand tools) having electric lamps for illuminating work areas are well known. Because of the small dimensions of such handpieces, particularly near their working ends, the usual practice is to mount such a lamp within the handle of the handpiece or within a threaded connector that joins the handpiece to the hose for supplying drive air and water. Such a construction is disclosed in coowned U.S. Pat. No. 4,600,384. Other U.S. Pat. Nos. revealing the state of the art are 4,330,274, 4,398,885, 4,375,964, 4,777,252, 4,334,863, and 4,514,169.

While such systems have been generally effective in operation, common disadvantages relate to the problems of lamp replacement. Ordinarily, disassembly of a number of parts is required to gain access for lamp removal and replacement. Even when such access is gained, the tiny lamps may be difficult to grasp for extraction and insertion. Sometimes lamp-containing modules must be removed and then either the lamps must be separated from the modules or the entire modules must be replaced. In the latter case, the difficulties of replacement may be reduced but only at the expense of substantially greater replacement costs.

Accordingly, a main aspect of this invention lies in providing a lamp-containing connector assembly and a lamp extraction/insertion tool which greatly simplify the task of lamp replacement while keeping to a minimum the time and cost involvements in such an operation. To remove a lamp, a dentist (or other operator) need only detach the handpiece from the connector and insert the head and stem portions of the tool into an exhaust air passage extending through the connector body. The exhaust air passage extends alongside the socket that contains the lamp and communicates with that socket through a slot or window that extends substantially the full length of the socket. The base portion of the lamp is provided with a lug that projects radially outwardly through the slot and into the exhaust air passage. Therefore, by the simple operation of fully inserting the head and stem portions of the tool into the exhaust air passage, then shifting the head laterally and withdrawing the tool, the lug may be easily engaged by the head portion and the lamp extracted from its socket as the tool is withdrawn.

In addition to providing access for lamp engagement and removal, the elongated slot slidably receives the lug in a way that orients the lamp so that proper mating engagement of electrical contacts is made when the lamp is fully inserted. Of particular importance is the fact that the slot also functions to allow cooling exhaust air to flow laterally from the exhaust air passage into the socket for cooling the bulb during operation. The heat absorbed by the air is then conducted away from the bulb through exhaust air passages or ports in the connector body.

In terms of structure, the connector body is generally cylindrical with a longitudinally-extending lamp-receiving socket and an exhaust air passage extending longitudinally through the body and alongside the socket. The exhaust air passage and socket communicate with each other through a narrow slot extending substantially the full length of the socket. A lamp received in the socket has bulb and base portions with the latter being provided with integral, radially-extending lug means dimensioned to extend transversely through the slot into the exhaust air passage and to be slidable along the slot during bulb insertion and extraction.

The lamp is generally cylindrical in configuration and has a diameter sufficiently smaller than the socket to provide an air flow space about the lamp when it is fully inserted. In addition, the connector body has an end wall defining at least one outflow passage at the base of the socket and a restricted exhaust port at the end of the exhaust air passage. The restriction in the exhaust air passage, the spacing about the lamp, and the outflow passage(s) at the base of the socket all contribute to insuring the circulation of cooling air about the lamp and the discharge of such air after being heated by the bulb.

The insertion/extraction tool has an elongated stem portion terminating at one end in a handle portion and at its opposite end in an enlarged head portion. The head portion is generally cylindrical and its diameter is smaller than the clearance space in the exhaust air passage between the end of the lug protruding into that passage and the wall of the passage directly opposite from the slot. Since the lug is spaced from the extreme end of the base portion of the lamp by a distance greater than the axial dimension of the head portion of the tool, the lug may be easily "hooked" by the head portion for extraction of the lamp from its socket. The combined length of the stem and head portions may be substantially the same, and in any event no less than, the distance between the face of the connector body and the restricted port near the distal end of the exhaust air passage, and the handle portion of the tool is preferably larger in cross section than the exhaust air passage. At the end of the tool opposite from the head portion, a stub portion may be provided having substantially the same diameter as that of the lamp, such stub being useful for seating the lamp in its socket.

Other features, advantages, and objects of the invention will become apparent from the specification and drawings.

DRAWINGS

DETAILED DESCRIPTION OF PREFERRED EMBODIMENT

Figure 1:
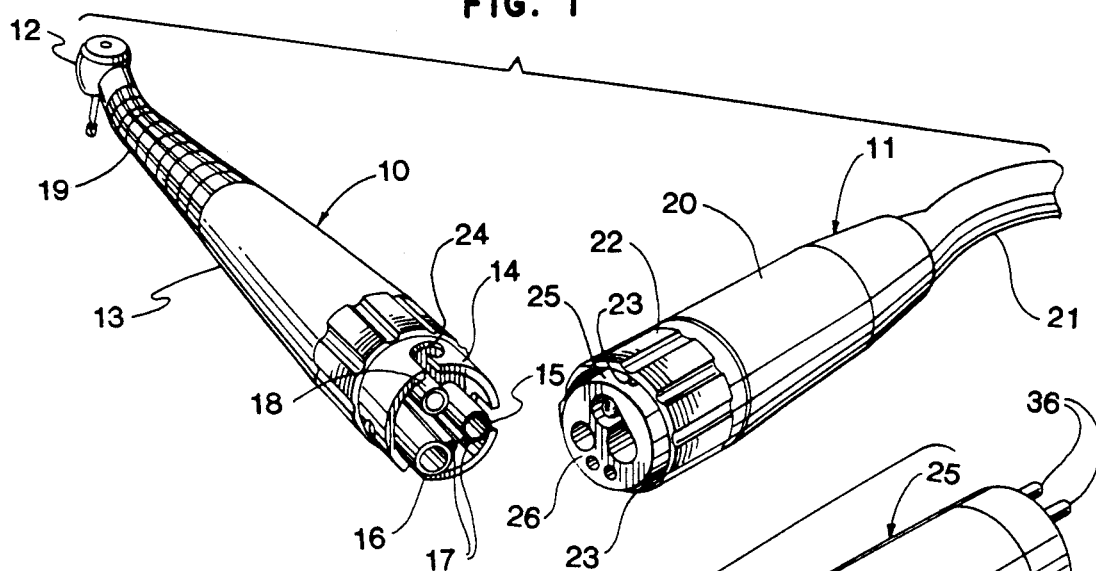
FIG. 1 is a perspective view showing a dental handpiece detached from a hose connector assembly embodying the present invention.

FIG. 1 depicts a dental handpiece 10 and a hose connector assembly 11 with the two parts uncoupled to reveal their mating elements. The handpiece is generally cnoventional, having a head 12, a handle 13, and a coupling sleeve or adapter 14. Handpiece 10 is typically a high speed handpiece of the air-driven turbine type and is provided with tubes 15 and 16 that protrude from its coupling end for drive and exhaust air, respectively. Other tubes 17 convey chip air and water, and the end of a fiberoptice light conductor or conduit 18 protrudes from the end of the handle within sleeve or adapter 14 for transmitting high-intensity light to terminal 19 at the working end of the handpiece.

The hose connector assembly 11 is preferably of the swivel type as generally disclosed in co-owned U.S. Pat. No. 4,553,938. Tapered housing 20 is joined to a supply and exhaust hose 21 which conveys drive air, chip air, electrical power for illumination, and water to the handpiece and which also carries away exhaust air from the handpiece. A collar 22 is rotatably connected to the housing an includes lugs 23 engagable with bayonet slots 24 of the coupling sleeve 14 when the two parts are joined together.

Within collar 22 and housing 20 is a generally cylindrical connector body 25. The body has an exposed end face 26 with openings 27-29 for receiving the end portions of tubes 15-17 of the handpiece 10. It will also be observed that a fifth opening 30 is located in end face 26 for receiving the stub of the handpiece's fiberoptic light conductor 18. Opening 30 is the entrance to a longitudinally-extending socket 31 that removably receives a miniature, high-intensity lamp 32.

Figure 2:
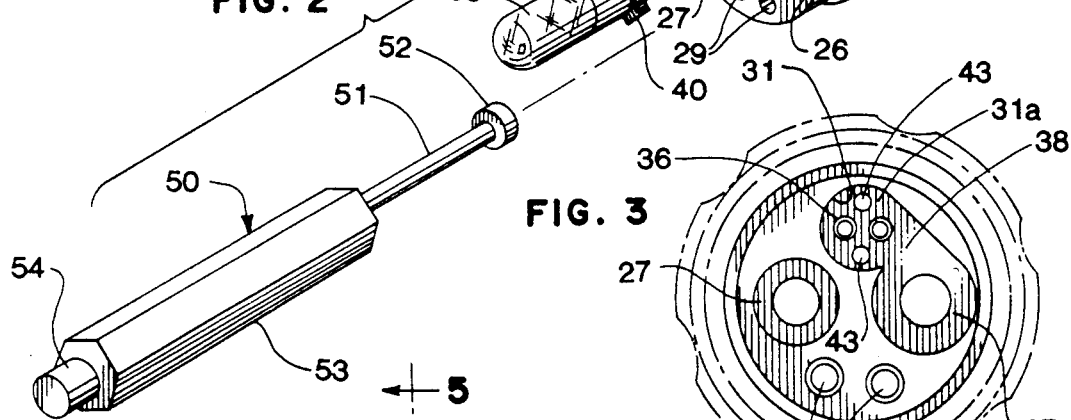
FIG. 2 is an exploded perspective view depicting the relationship between the cylindrical body of the connector assembly, a lamp, and a tool for insertion and removal of the lamp.
Figure 5:
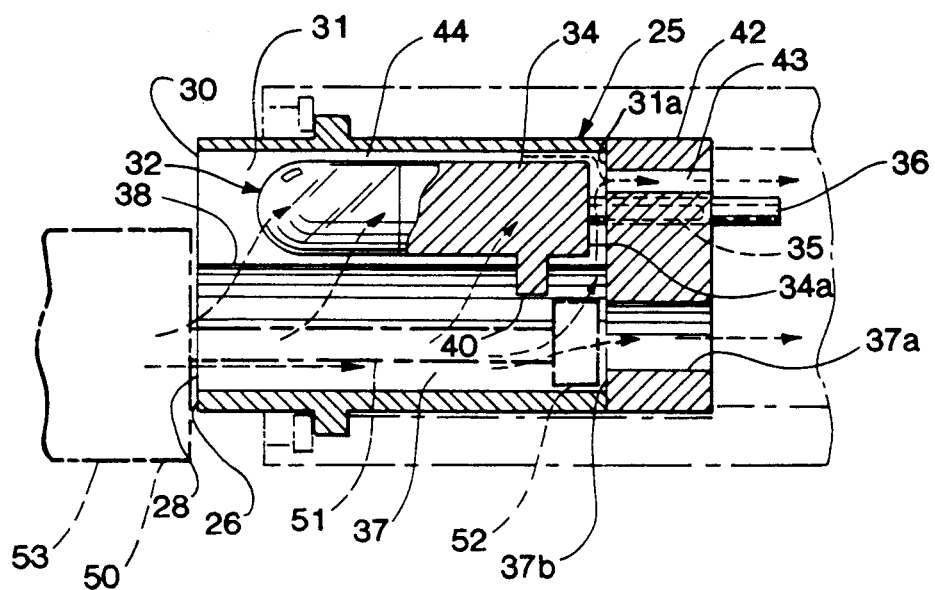
FIG. 5 is a longitudinal cross sectional view of the connector body and lamp taken along line 5—5 of FIG. 4.

The lamp includes a bulb portion 33 and a base portion 34 and, as shown in FIGS. 2 and 5, is generally cylindrical in configuration. A pair of conductive prongs 35 project from the end of the base portion and are received within electrically conductive tubes or sleeves 36 secured to the end of the connector body 25 within housing 20. The tubes are in turn joined to wires (not shown) leading from a suitable electrical power supply and extending through hose 21.

Figure 3:
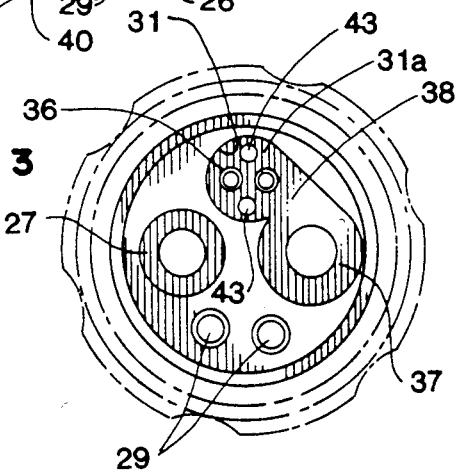
FIG. 3 is an enlarged end view of the connector body with surrounding parts of the connector assembly being depicted in phantom.

Of particular importance is the fact that exhaust air passage 37 extends completely through connector body 25, is disposed alongside socket 31, and communicates with that socket through a longitudinally-extending slot or window 38 (FIGS. 3,5). The slot 38 extends substantially the full length of socket 31 and is of uniform width throughout its entire extent.

Figure 4:
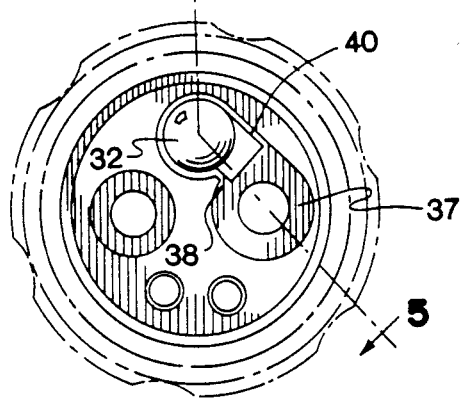
FIG. 4 is an end view similar to FIG. 3 but showing the connector body with a lamp inserted therein.
Figure 6:
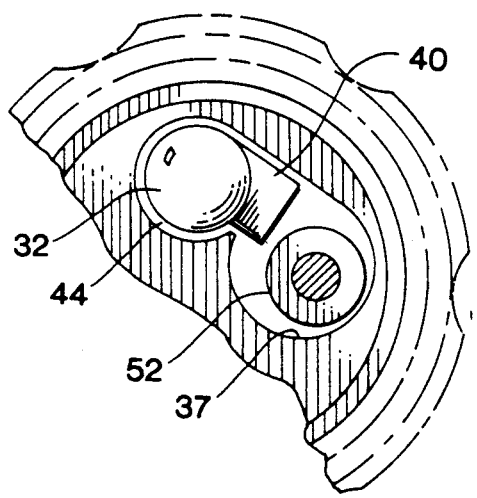
FIG. 6 is a further enlarged fragmentary end view similar to FIG. 4 but showing a lamp extracting tool inserted into the exhaust air passage.
Figure 7:
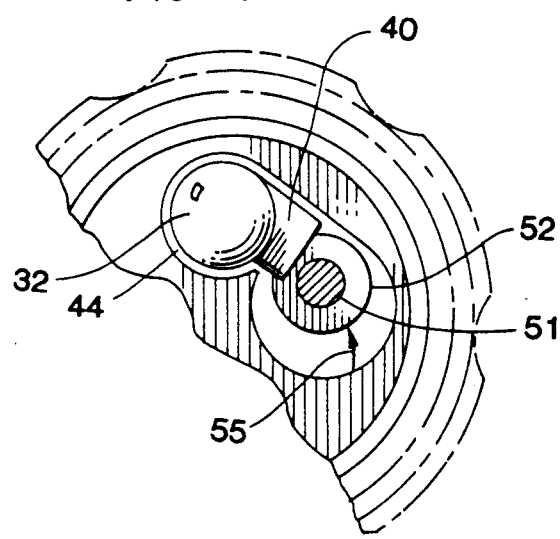
FIG. 7 is a fragmentary end view similar to FIG. 6 but showing the tool shifted laterally for capturing and extracting the lamp.

The width of the slot 38 is only slightly greater than the width of a lug 40 projecting laterally or radially from the base portion 34 of lamp 32. When the lamp is inserted into its socket, lug 40 projects through the slot into exhaust air passage 37 as shown most clearly in FIGS. 4, 6, and 7. Since the clearance between the lug and the sides of the slot is slight, the slot orients a bulb being inserted into its socket so that its prongs 35 will be properly aligned with the tubes 36 with which they are to make electrical contact. During insertion, the edges of lug 40 slidably engage the sides or edges of the slot 38 to guide the bulb and maintain it at the proper angle of rotation.

Connector body 25 also includes an end wall 42 that defines a restricted or reduced portion of exhaust air portion 37a of exhaust air passage 37. In addition, wall 42 defines the end or inner wall of socket 31. However, as shown clearly in FIG. 3, air outlet passages 43 extend longitudinally through the end wall at the base of the socket. At least one such passage 43 should be provided; in the embodiment illustrated, a pair of such passages are shown and, if desired, a greater number may be provided.

The cylindrical lamp 32 is sufficiently smaller in diameter than socket 31 to define an annular space 44 for the circulation of air about the sides of the lamp. Exhaust air from passage 37 may therefore enter the socket along its full length, through longitudinal slot 38, circulate about the lamp, and exit from the socket through outlet passages 43, as indicated by dashed arrows in FIG. 5. Since the air that cools the bulb is exhaust air rather than drive air, the heat absorbed by such air is carried away rather than towards the handpiece. Slight pressurization of the air within the socket results from the fact that the exhaust air passage is provided with a restricted end portion 37a, thereby insuring that a portion of the exhaust air will be circulated through the socket 31 about lamp 32.

It will be observed from FIG. 5 that socket 31 has an end face 31a and that when lamp 32 is fully inserted as shown, the terminal face 34a of the lamp's base portion 34 is spaced from the end face 31a of the socket. In the illustration given, such spacing is achieved by means of tubes 36 which protrude slightly into the socket 31 and serve as stops to limit the extent of insertion of the lamp; however, it is believed apparent that other stop means might be provided for limiting the extent of bulb insertion.

Lug 40 projects laterally from the base portion at a point spaced longitudinally from the terminal face 34a of that base portion. Therefore, when the bulb is fully inserted, lug 40 is spaced from the end face 31a and from coplanar annular shoulder 37b of exhaust air passage 37. Such spacing permits the lug to be captured or caught for bulb extraction by means of an insertion/extraction tool 50 shown most clearly in FIG. 2.

Tool 50 has an elongated stem portion 51, an enlarged head portion 52 at one end of the stem portion, and an elongated handle 53 coaxial with the stem and projecting from the stem's opposite end. The handle portion 53 is preferably hexagonal in cross section so that the tool will not roll freely when placed on a support surface. At the end of the handle opposite from stem portion 51 is a cylindrical stub portion 54 having a diameter approximating that of cylindrical lamp 32. The length of the stub portion is the same as the extent of setback of lamp 32 when the lamp is fully inserted in socket 31. Thus, the stub portion 54 may be used effectively in urging the lamp into fully seated position within its socket.

As depicted in FIGS. 2 and 5, the cross sectional dimensions of handle portion 53 are substantially larger than the respective entrances 30 and 28 to socket 31 and exhaust air passage 37. The cylindrical head portion, however, has a diameter appreciable smaller than that of either the socket or the main portion of exhaust air passage 37, although it is larger in diameter than the reduced portion 37a of the exhaust air passage. More specifically, the diameter of the head portion is less than clearance distance between the end of lug 40 and the wall surface of exhaust air passage 37 diametrically opposite from that lug. Since the axial dimension of the head portion 52 is less than the axial distance between the lug 40 of a fully inserted bulb and the annular shoulder 37b in exhaust passage 37, there is sufficient space in the exhaust passage to permit the head portion 52 of the tool to be inserted past lug 40 (see FIGS. 5 and 6). Thereafter, by shifting the tool laterally as indicated by arrow 55 in FIG. 7, the annular rear face of the head portion may be shifted behind lug 40 to catch or capture the lug so that when the tool is withdrawn the bulb 32 will be extracted from its socket.

To facilitate such extraction, the combined length of head 52 and stem 51 should equal the length of exhaust air passage 37 measured between entrance 28 and annular shoulder 37b. In any event, the length of the stem portion must always exceed the distance between entrance 28 and the surface of lug 40 facing annular shoulder 37b. When the head and stem portions of the tool are inserted into the exhaust passage until handle portion 50 abuts end face 26 of body 25, such abuting engagement serves to indicate to the user that by laterally shifting the tool in the direction of the lamp socket the lug of the lamp will be engaged to cause lamp extraction when the tool is pulled straight out of the exhaust passage.

Slot 38 therefore performs multiple functions. It places socket 31 in direct communication with exhaust passage 37 for the full length of that socket, thereby permitting cooling exhaust air to flow over an inserted lamp as indicated by the dashed arrows in FIG. 5. Because the slot has a uniform width slightly greater than the width of lug 40, it serves as a guide slot for assisting a user in properly orienting bulb 32 for insertion into its socket and for guiding subsequent movement of the lamp to bring its electrical contacts or pins 35 into alignment with electrical contacts (tubes) 36. Since the lug extends through the slot into the exhaust passage, such lug may be readily engaged by tool 50 when lamp removal is desired.

While in the foregoing, an embodiment of the invention has been disclosed in considerable detail for purposes of illustration, it will be understood by those skilled in the art that many of these details may be varied without departing from the spirit and scope of the invention.

I claim:

1. In combination, a generally cylindrical connector body for conducting air to and from a turbine-driven dental handpiece; said body having a longitudinally-extending socket and having an end face providing a socket entrance; said body also having an exhaust air passage extending longitudinally therethrough; said passage being located alongside said socket and communicating with said socket through a slot extending substantially the full length of said socket; and a lamp having a bulb portion and a base portion slidably and removably received in said socket for insertion and extraction of said lamp through said entrance; said base portion having lug means projecting laterally through said slot into said exhaust air passage for engagement by a tool insertable into said exhaust passage for extraction of said lamp from said socket.

2. The combination of claim 1 in which said slot is of substantially uniform width throughout its length.

3. The combination of claim 1 in which said body includes an inner end wall for said socket.

4. The combination of claim 3 in which said lamp has a maximum cross sectional dimension sufficiently smaller than said socket to define an air flow space therebetween.

5. The combination of claim 3 in which said inner end wall and said base portion of said lamp have electrical contact means engagable with each other when said lamp is fully inserted in said socket; said lug means having a width only slightly less than that of said slot for orienting said lamp and thereby aligning said contact means for mutual engagement when said lamp is inserted into said socket.

6. The combination of claims 4 or 5 in which said inner end wall includes at least one exhaust air passage therethrough.

7. The combination of claim 6 in which said exhaust air passage is reduced in cross sectional area at the end of said body opposite from said end face to define an annular shoulder within said passage.

8. The combination of claim 4 in which said lamp is generally cylindrical in shape.

9. The combination of claim 8 in which said lug means comprises a radial projection from said base portion; said base portion including a terminal face at the end of said base portion opposite from said bulb portion; said projection being spaced longitudinally from said terminal face.

10. The combination of claim 9 in which said projection is an integral part of said base portion.

11. The combination of claim 1 including a tool having an elongated stem portion, a handle portion at one end of said stem portion, and an enlarged head portion at the opposite end of said stem portion; said head portion providing a shoulder facing towards said stem and handle portions for engaging and catching said lug means of said lamp when said tool is inserted into said exhaust air passage.

12. The combination of claim 11 in which said head portion is generally cylindrical in shape; said head portion being coaxial with and substantially larger in diameter than said stem portion.

13. The combination of claim 12 in which said exhaust passage is reduced in cross sectional area to define a restricted exhaust opening at the end of said body opposite from said end face.

14. The combination of claim 13 in which said head has a diameter larger than said restricted exhaust opening of said passage.

15. The combination of claim 12 in which said lug means comprises a radial projection from said base portion; said projection having a free end spaced from a surface of said exhaust air passage opposite from said slot a predetermined clearance distance; said head portion of said tool having a diameter less than said clearance distance.

16. The combination of claim 13 in which said stem portion and said head portion have a combined length substantially the same as the distance between said end face of said body and said restricted exhaust opening of said exhaust air passage.

17. The combination of claim 16 in which said handle portion is substantially larger in cross section than said exhaust air passage.

18. The combination of claim 17 in which said handle portion is of hexagonal cross sectional configuration.

19. The combination of claim 11 in which said tool also includes a stub portion projecting from the end of said handle opposite from said stem portion; said stub portion having a diameter less than said socket.

20. The combination of claim 19 in which there is a setback of said bulb portion from said end face of said body when said lamp is fully inserted into said socket; said stub portion having a length substantially equal to said setback.

* * * * *